United States Patent
Gemert et al.

[11] Patent Number: 5,961,892
[45] Date of Patent: Oct. 5, 1999

[54] POLYALKOXYLATED NAPHTHOPYRANS

[75] Inventors: Barry Van Gemert; Kevin J. Stewart, both of Murrysville, Pa.

[73] Assignee: PPG Industries Ohio, Inc., Cleveland, Ohio

[21] Appl. No.: 09/151,982

[22] Filed: Sep. 11, 1998

[51] Int. Cl.[6] .......................... G02B 5/23; C07D 311/92
[52] U.S. Cl. .......................... 252/586; 549/389; 549/58; 549/60; 549/331; 549/362; 549/382; 548/454; 546/280.4; 546/281.1; 546/282.7
[58] Field of Search .......................... 252/586; 549/389, 549/58, 60, 331, 362, 382; 548/454; 546/280.4, 281.1, 282.7

[56] References Cited

U.S. PATENT DOCUMENTS

| | | | |
|---|---|---|---|
| 4,719,296 | 1/1988 | Irie et al. | 544/71 |
| 5,458,814 | 10/1995 | Kumar et al. | 252/586 |
| 5,466,398 | 11/1995 | Van Gemert et al. | 252/586 |
| 5,488,119 | 1/1996 | Fischer-Reimann et al. | 552/201 |
| 5,520,853 | 5/1996 | Rickwood et al. | 252/586 |
| 5,552,091 | 9/1996 | Kumar | 252/586 |
| 5,573,712 | 11/1996 | Kumar et al. | 252/586 |
| 5,578,252 | 11/1996 | Van Gemert | 252/586 |
| 5,585,042 | 12/1996 | Knowles | 252/586 |
| 5,637,262 | 6/1997 | Van Gemert et al. | 252/586 |
| 5,645,767 | 7/1997 | Van Gemert | 252/586 |
| 5,658,500 | 8/1997 | Kumar et al. | 252/586 |
| 5,658,501 | 8/1997 | Kumar et al. | 252/586 |
| 5,744,070 | 4/1998 | Kumar | 252/586 |
| 5,753,146 | 5/1998 | Van Gemert et al. | 252/586 |

FOREIGN PATENT DOCUMENTS

| | | |
|---|---|---|
| 3-100091 | 4/1991 | Japan . |
| 3-91578 | 4/1991 | Japan . |
| WO 97/05213 | 2/1997 | WIPO . |

OTHER PUBLICATIONS

Bradshaw, J.S., et al., "Synthesis of Macrocyclic Acetals Containing Lipophilic Substituents", Tetrahedron, vol. 43, No. 19, pp. 4271–4276, 1987.

Organic Synthesis, vol. 31, pp. 90–92, John Wiley & Sons, Inc., New York, 1951.

*Primary Examiner*—Philip Tucker
*Attorney, Agent, or Firm*—Frank P. Mallak; Irwin M. Stein

[57] ABSTRACT

Described are novel photochromic polyalkoxylated naphthopyran compounds, examples of which are certain 2H-naphtho[1,2-b]pyrans, 3H-naphtho[2,1-b]pyrans and indeno[2,1-f]naphtho[1,2-b]pyrans, each having at least one polyalkoxylated substituent of from 2 to 50 alkoxy units per substituent. Specific substituents may also be present on the naphtho, indeno and pyrano portions of the compounds. These compounds may be represented by the following graphic formulae:

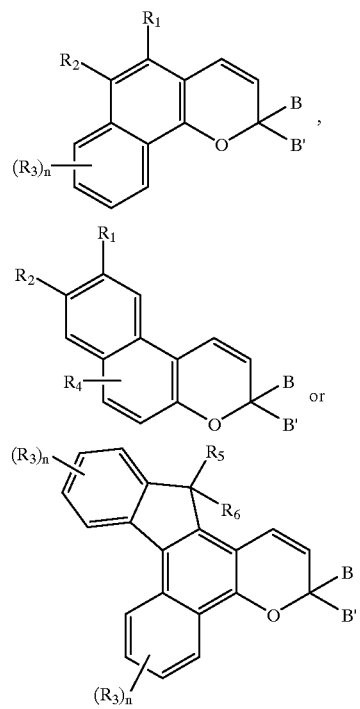

19 Claims, No Drawings

POLYALKOXYLATED NAPHTHOPYRANS

DESCRIPTION OF THE INVENTION

The present invention relates to certain novel naphthopyran compounds. More particularly, this invention relates to photochromic polyalkoxylated naphthopyran compounds and to compositions and articles containing such novel photochromic compounds. When exposed to electromagnetic radiation containing ultraviolet rays, such as the ultraviolet radiation in sunlight or the light of a mercury lamp, many photochromic compounds exhibit a reversible change in color. When the ultraviolet radiation is discontinued, such a photochromic compound will return to its original color or colorless state.

Various classes of photochromic compounds have been synthesized and suggested for use in applications in which a sunlight-induced reversible color change or darkening is desired. U.S. Pat. No. 3,567,605 (Becker) describes a series of pyran derivatives, including certain benzopyrans and naphthopyrans.

U.S. Pat. No. 5,458,814 describes photochromic 2,2-di-substituted-5,6-substituted-2H-naphtho[1,2-b]pyran compounds primarily for use in lenses and other plastic transparencies. These compounds have an acceptable fade rate in addition to a high activated intensity and a high coloration rate. U.S. Pat. No. 5,585,042 discloses 3,3-di-substituted-8-substituted-3H-naphtho[2,1-b]pyran compounds for similar uses. These compounds exhibit an improved solar response, a higher activating wavelength than unsubstituted naphthopyrans, and an acceptable bleach or fade rate. U.S. Pat. No. 5,645,767 describes photochromic indeno[2,1-f]naphtho[1,2-b]pyrans having a high activated intensity, an acceptable fade rate and high coloration rate.

Although 3H-naphtho[2,1-b]pyrans, 2H-naphtho[1,2-b]pyrans and indeno[2,1-f]naphtho[1,2-b]pyrans of good intensity and reasonable fade are currently available, it is desirable to enhance the fade rate of the photochromic compound without changing its activated color. This may be done to either match the same properties of complementary photochromic compounds or enable the use of such compounds in rigid plastic matrices wherein the activation/fade kinetics of photochromic compounds are frequently slowed.

In accordance with the present invention, there have been discovered novel photochromic compounds; namely, certain 2H-naphtho[1,2-b]pyrans, 3H-naphtho[2,1-b]pyrans and indeno[2,1-f]naphtho[1,2-b]pyrans that have at least one polyalkoxylated substituent. The presence of the polyalkoxylated substituent results in an improved fade or bleach rate as compared to naphthopyrans having a single alkoxy substituent. of equal importance, activated colors are not changed with this substitution. Depending on the location of the polyalkoxylated substituent, certain other substituents may also be present on the naphtho, pyrano and indeno portions of the aforedescribed compounds.

DETAILED DESCRIPTION OF THE INVENTION

In accordance with the present invention, it has been discovered that the fade rate of certain photochromic 2H-naphtho[1,2-b]pyrans, 3H-naphtho[2,1-b]pyrans and indeno[2,1-f]naphtho[1,2-b]pyrans may now be improved by including at least one polyalkoxylated substituent on such compounds. The polyalkoxylated substituent may have from 2 to 50 alkoxy units and may be located on the naphtho or indeno portion and/or on the pyrano portion of the naphthopyran.

The naphthopyrans of the present invention also may have certain other substituents. Specifically, the 2H-naphthopyrans may have substituents at the 5 and 6 positions and may have additional substituents at the 7, 8, 9 and 10 positions; the 3H naphthopyrans may have substituents at the 8 and 9 positions and may have additional substituents at the 5 and 6 positions; and the indeno-fused naphthopyrans may have certain substituents at the 5, 6, 7, 8, 9, 10, 11, 12 or 13 positions. The aforedescribed naphthopyrans may be represented by graphic formulae I, II and III respectively in which the internal ring numbers 1 through 13 identify the numbering of the ring atoms of the naphthopyrans and letters a through n represent the sides of the naphthopyran rings. In the definition of the substituents shown in the following graphic formulae I, II and III, like symbols have the same meaning unless stated otherwise.

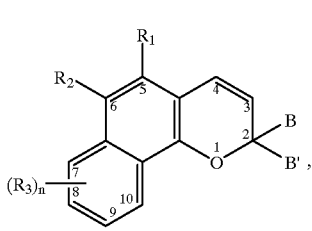

I

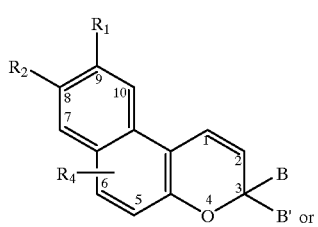

II

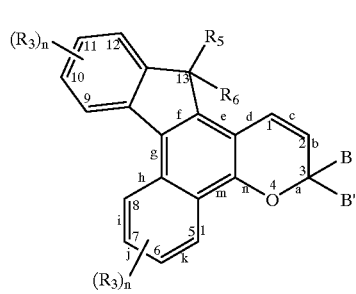

III

In graphic formulae I, II and III, $R_1$, $R_2$, $R_3$, $R_4$, $R_5$ or $R_6$ may be the group R represented by the formula:

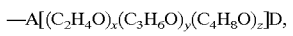

—A[$(C_2H_4O)_x(C_3H_6O)_y(C_4H_8O)_z$]D, wherein —A is —C(O)O, —CH$_2$O or —O and D is $C_1$–$C_3$ alkyl; provided, however, that only one R group is present on the naphtho or indeno portion of the naphthopyran. The group, —$(C_2H_4O)_x$—, represents poly(ethylene oxide); —$(C_3H_6O)_y$—, represents poly(propylene oxide); and, —$(C_4H_8O)_z$—, represents poly(butylene oxide). When used in combination, the poly(ethylene oxide), poly(propylene oxide) and poly(butylene oxide) groups of R may be in a random or block order within the R moiety. The letters x, y and z are each a number between 0 and 50 and the sum of x, y and z is between 2 and 50. The sum of x, y and z may be any number that falls within the range of 2 to 50, e.g., 2, 3, 4 . . . 50. This sum may also range from any lower number to any higher number within the range of 2 to 50, e.g., 6 to 50, 31 to 50. The numbers for x, y, and z are average values and can be partial numbers, e.g., 9.5.

Preferably, $R_1$, $R_2$, $R_3$, $R_4$, $R_5$ or $R_6$ is the group R wherein x and y are each a number between 0 and 50, z is 0 and the sum of x and y is between 2 and 50, and more preferably, x is a number between 2 and 50, and y and z are each 0.

Alternatively, the substituents $R_1$, $R_2$, $R_3$, $R_4$, $R_5$ or $R_6$ in graphic formulae I, II and III may be a group other than R; provided, that one of such substituents is the group R. $R_1$ may be hydrogen, $C_1$–$C_3$ alkyl or the group, —C(O)W, W being —$OR_7$, —N($R_8$)$R_9$, piperidino or morpholino, wherein $R_7$ is allyl, $C_1$–$C_6$ alkyl, phenyl, mono($C_1$–$C_6$)alkyl substituted phenyl, mono($C_1$–$C_6$)alkoxy substituted phenyl, phenyl($C_1$–$C_3$)alkyl, mono($C_1$–$C_6$)alkyl substituted phenyl ($C_1$–$C_3$)alkyl, mono($C_1$–$C_6$)alkoxy substituted phenyl ($C_1$–$C_3$)alkyl, $C_1$–$C_6$ alkoxy($C_2$–$C_4$)alkyl or $C_1$–$C_6$ haloalkyl; $R_8$ and $R_9$ are each selected from the group consisting of $C_1$–$C_6$ alkyl, $C_5$–$C_7$ cycloalkyl, phenyl and mono- or di-substituted phenyl, said phenyl substituents being $C_1$–$C_6$ alkyl or $C_1$–$C_6$ alkoxy, and said halo substituent being chloro or fluoro. Preferably, $R_1$ is the group, —C(O)W, W being —$OR_7$ or —N($R_8$)$R_9$, wherein $R_7$ is $C_1$–$C_4$ alkyl, phenyl, mono($C_2$–$C_4$) alkyl substituted phenyl, mono($C_1$–$C_4$)alkoxy substituted phenyl, phenyl($C_1$–$C_2$) alkyl, mono($C_1$–$C_4$)alkyl substituted phenyl($C_1$–$C_2$)alkyl, mono($C_1$–$C_4$)alkoxy substituted phenyl($C_1$–$C_2$)alkyl, mono ($C_1$–$C_4$)alkoxy($C_2$–$C_3$)alkyl or $C_1$–$C_4$ haloalkyl; $R_8$ and $R_9$ are each selected from the group consisting of $C_1$–$C_4$ alkyl, $C_5$–$C_7$ cycloalkyl, phenyl and mono- or di-substituted phenyl, said phenyl substituents being $C_1$–$C_4$ alkyl or $C_1$–$C_4$ alkoxy, and said halo substituents being chloro or fluoro. More preferably, $R_1$ is the group, —C(O)W, W being the group —$OR_7$, wherein $R_7$ is a $C_1$–$C_3$ alkyl.

$R_2$, each $R_3$, and $R_4$ may be selected from the group consisting of hydrogen, $C_1$–$C_6$ alkyl, $C_3$–$C_7$ cycloalkyl, phenyl, mono- or di-substituted phenyl and the groups —$OR_{10}$ and —OC(O)$R_{10}$, wherein $R_{10}$ is $C_1$–$C_6$ alkyl, phenyl($C_1$–$C_3$)alkyl, mono($C_1$–$C_6$)alkyl substituted phenyl ($C_1$–$C_3$)alkyl, mono($C_1$–$C_6$)alkoxy substituted phenyl ($C_1$–$C_3$)alkyl, $C_1$–$C_6$ alkoxy($C_2$–$C_4$)alkyl, $C_3$–$C_7$ cycloalkyl or mono($C_1$–$C_4$)alkyl substituted $C_3$–$C_7$ cycloalkyl, n is selected from the integers 0, 1 and 2 and the phenyl substituents are the same as for $R_1$. Preferably, $R_2$, each $R_3$, and $R_4$ are selected from the group consisting of hydrogen, $C_1$–$C_3$ alkyl, $C_3$–$C_5$ cycloalkyl, phenyl, mono- or di-substituted phenyl and the group —$OR_{10}$, wherein $R_{10}$ is $C_1$–$C_4$ alkyl, phenyl($C_1$–$C_2$)alkyl, mono($C_1$–$C_4$)alkyl substituted phenyl($C_1$–$C_2$)alkyl, mono($C_1$–$C_4$)alkoxy substituted phenyl($C_1$–$C_2$)alkyl, $C_1$–$C_4$ alkoxy($C_2$–$C_4$)alkyl, $C_5$–$C_7$ cycloalkyl or mono($C_1$–$C_3$)alkyl substituted $C_5$–$C_7$ cycloalkyl and the phenyl substituents are $C_1$–$C_3$ alkyl or $C_1$–$C_3$ alkoxy. More preferably, $R_2$, each $R_3$, and $R_4$ are selected from the group consisting of hydrogen, $C_1$–$C_3$ alkyl, phenyl, mono- or di-substituted phenyl and the group —$OR_{10}$, wherein $R_{10}$ is $C_1$–$C_3$ alkyl and the phenyl substituents are methyl or methoxy.

$R_5$ and $R_6$ may together form an oxo group, a spiroheterocyclic group containing 2 oxygen atoms and 3 to 6 carbon atoms including the spirocarbon atom, which may be represented by the expression (—O—($C_2$–$C_5$ alkanediiyl)—O—), e.g., spiro-1,3-dioxolane-2, spiro-1,3-dioxane-2, etc., or $R_5$ and $R_6$ may each be hydrogen, hydroxy, $C_1$–$C_6$ alkyl, $C_3$–$C_7$ cycloalkyl, allyl, phenyl, mono-substituted phenyl, benzyl, mono-substituted benzyl, chloro, fluoro, the group —C(O)X, wherein X is hydroxy, $C_1$–$C_6$ alkyl, $C_1$–$C_6$ alkoxy, phenyl, mono-substituted phenyl, amino, mono ($C_1$–$C_6$)alkylamino, or di($C_1$–$C_6$)alkylamino, e.g., dimethylamino, methylpropylamino, etc., or $R_5$ and $R_6$ may each be the group, —$OR_{11}$, wherein $R_{11}$ is $C_1$–$C_6$ alkyl, phenyl($C_1$–$C_3$)alkyl, mono($C_1$–$C_6$)alkyl substituted phenyl ($C_1$–$C_3$)alkyl, mono($C_1$–$C_6$)alkoxy substituted phenyl ($C_1$–$C_3$)alkyl, $C_1$–$C_6$ alkoxy($C_2$–$C_4$)alkyl, $C_3$–$C_7$ cycloalkyl, mono($C_1$–$C_4$)alkyl substituted $C_3$–$C_7$ cycloalkyl, $C_1$–$C_6$ chloroalkyl, $C_1$–$C_6$ fluoroalkyl, allyl, the group, —CH($R_{12}$)Y, wherein $R_{12}$ is hydrogen or $C_1$–$C_3$ alkyl and Y is CN, $CF_3$, or COO$R_{13}$, and $R_{13}$ is hydrogen or $C_1$–$C_3$ alkyl, or $R_{11}$ is the group, —C(O)Z, wherein Z is hydrogen, $C_1$–$C_6$ alkyl, $C_1$–$C_6$ alkoxy, the unsubstituted, mono- or di-substituted aryl groups, phenyl or naphthyl, phenoxy, mono- or di-($C_1$–$C_6$)alkyl substituted phenoxy, mono- or di-($C_1$–$C_6$)alkoxy substituted phenoxy, mono- or di-($C_1$–$C_6$)alkoxy substituted phenoxy, amino, mono ($C_1$–$C_6$)alkylamino, di($C_1$–$C_6$)alkylamino, phenylamino, mono- or di($C_1$–$C_6$)alkyl substituted phenylamino, or mono- or di-($C_1$–$C_6$)alkoxy substituted phenylamino, each of the aforedescribed phenyl, benzyl and aryl group substituents being $C_1$–$C_6$ alkyl or $C_1$–$C_6$ alkoxy.

More preferably, $R_5$ and $R_6$ are each selected from the group consisting of hydrogen, hydroxy, $C_1$–$C_4$ alkyl, $C_3$–$C_6$ cycloalkyl, chloro, fluoro and the group, —$OR_{11}$, wherein $R_{11}$ is $C_1$–$C_3$ alkyl, phenyl($C_1$–$C_2$)alkyl, mono($C_1$–$C_3$)alkyl substituted phenyl($C_1$–$C_3$)alkyl, mono($C_1$–$C_3$)alkoxy substituted phenyl($C_1$–$C_3$)alkyl, $C_1$–$C_3$ alkoxy($C_2$–$C_4$)alkyl, $C_1$–$C_3$ chloroalkyl, $C_1$–$C_3$ fluoroalkyl, the group, —H($R_{12}$)Y, wherein $R_{12}$ is hydrogen or $C_1$–$C_2$ alkyl and Y is CN or COO$R_{13}$, $R_{13}$ being hydrogen or $C_1$–$C_2$ alkyl, or $R_{11}$ is the group, —C(O)Z, wherein Z is hydrogen, $C_1$–$C_3$ alkyl, $C_1$–$C_3$ alkoxy, phenyl, naphthyl, the mono-substituted aryl groups, phenyl or naphthyl, phenoxy, mono- or di-($C_1$–$C_3$)alkyl substituted phenoxy, mono- or di-($C_1$–$C_3$)alkoxy substituted phenoxy, mono($C_1$–$C_3$) alkyl amino, phenylamino, mono- or di-($C_1$–$C_3$)alkyl substituted phenylamino, or mono- or di- ($C_1$–$C_3$)alkoxy substituted phenylamino, each of said aryl group substituents being $C_1$–$C_3$ alkyl or $C_1$–$C_3$ alkoxy. Most preferably, $R_5$ and $R_6$ are each hydrogen, hydroxy, $C_1$–$C_4$ alkyl or the group, —$OR_{11}$, wherein $R_{11}$ is $C_1$–$C_3$ alkyl.

B an B' are each selected from the group consisting of: (a) mono R-substituted phenyl represented by the following graphic formula IV:

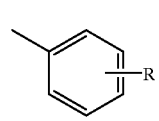

IV wherein the group R is the same as previously described; (b) the unsubstituted, mono-, di- and tri-substituted aryl groups, phenyl and naphthyl; (c) the unsubstituted, mono- and di-substituted heteroaromatic groups pyridyl, furanyl, benzofuran-2-yl, benzofuran-3-yl, thienyl, benzothien-2-yl, benzothien-3-yl, dibenzofuranyl, dibenzothienyl, carbazolyl an d fluorenyl, each of said aryl and heteroaromatic substituents in (b) and (c) being selected from the group consisting of hydroxy, aryl, i.e., phenyl and naphthyl, mono ($C_1$–$C_6$)alkoxyaryl, di($C_1$–$C_6$)alkoxyaryl, mono($C_1$–$C_6$) alkylaryl, di($C_1$–$C_6$)alkylaryl, chloroaryl, fluoroaryl, $C_3$–$C_7$ cycloalkylaryl, $C_3$–$C_7$ cycloalkyl, $C_3$–$C_7$ cycloalkyloxy, $C_3$–$C_7$ cycloalkyloxy($C_1$–$C_6$)alkyl, $C_3$–$C_7$ cycloalkyloxy ($C_1$–$C_6$)alkoxy, aryl($C_1$–$C_6$)alkyl, aryl($C_1$–$C_6$)alkoxy, aryloxy, aryloxy($C_1$–$C_6$)alkyl, aryloxy($C_1$–$C_6$)alkoxy, mono- and di-($C_1$–$C_6$)alkylaryl($C_1$–$C_6$)alkyl, mono- and di-($C_1$–$C_6$)alkoxyaryl($C_1$–$C_6$)alkyl, mono- and di-($C_1$–$C_6$) alkylaryl($C_1$–$C_6$)alkoxy, mono- and di-($C_1$–$C_6$)alkoxyaryl ($C_1$–$C_6$)alkoxy, amino, mono($C_1$–$C_6$)alkylamino, di($C_1$–$C_6$) alkylamino, diarylamino, N-($C_1$–$C_6$)alkylpiperazino, N-arylpiperazino, aziridino, indolino, piperidino, arylpiperidino, morpholino, thiomorpholino, tetrahydroquinolino, tetrahydroisoquinolino, pyrryl, $C_1$–$C_6$ alkyl, $C_1$–$C_6$ chloroalkyl, $C_1$–$C_6$ fluoroalkyl, $C_1$–$C_6$ alkoxy, mono($C_1$–$C_6$)alkoxy($C_1$–$C_4$)alkyl, acryloxy, methacryloxy, bromo, chloro and fluoro; (d) the groups represented by the following graphic formulae VA and VB:

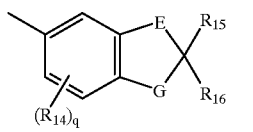

VA

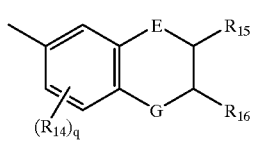

VB wherein E is carbon or oxygen and G is oxygen or substituted nitrogen, provided that when G is substituted nitrogen, E is carbon, said nitrogen substituents being selected from the group consisting of hydrogen, $C_1$–$C_6$ alkyl and $C_2$–$C_6$ acyl; each $R_{14}$ is $C_1$–$C_6$ alkyl, $C_1$–$C_6$ alkoxy, hydroxy, chloro or fluoro; $R_{15}$ and $R_{16}$ are each hydrogen or $C_1$–$C_6$ alkyl; and q is the integer 0, 1 or 2; (e) $C_1$–$C_6$ alkyl, $C_1$–$C_6$ chloroalkyl, $C_1$–$C_6$ fluoroalkyl, $C_1$–$C_6$ alkoxy($C_1$–$C_4$)alkyl; and (f) the group represented by the following graphic formula VC:

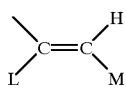

VC wherein L is hydrogen or $C_1$–$C_4$ alkyl and M is selected from the unsubstituted, mono-, and di-substituted members of the group consisting of naphthyl, phenyl, furanyl and thienyl, each of said group substituents being $C_1$–$C_4$ alkyl, $C_1$–$C_4$ alkoxy, fluoro or chloro.

Preferably, B and B' are each selected from the group consisting of: (a) mono R-substituted phenyl; (b) phenyl, mono-substituted and di-substituted phenyl; (c) the unsubstituted, mono- and di-substituted heteroaromatic groups furanyl, benzofuran-2-yl, thienyl, benzothien-2-yl, dibenzofuran-2-yl, and dibenzothien-2-yl, each of said phenyl and heteroaromatic substituents in (b) and (c) being selected from the group consisting of hydroxy, aryl, arlyoxy, aryl($C_1$–$C_3$)alkyl, amino, mono($C_1$–$C_3$)alkylamino, di($C_1$–$C_3$)alkylamino, N-($C_1$–$C_3$)alkylpiperazino, indolino, piperidino, morpholino, pyrryl, $C_1$–$C_3$ alkyl, $C_1$–$C_3$ chloroalkyl, $C_1$–$C_3$ fluoroalkyl, $C_1$–$C_3$ alkoxy, mono ($C_1$–$C_3$)alkoxy($C_1$–$C_3$)alkyl, chloro and fluoro; (d) the groups represented by graphic formulae VA and VB wherein E is carbon and G is oxygen, $R_{14}$ is $C_1$–$C_3$ alkyl or $C_1$–$C_3$ alkoxy; $R_{15}$ and $R_{16}$ are each hydrogen or $C_1$–$C_4$ alkyl; and q is 0 or 1; (e) $C_1$–$C_4$ alkyl; (f) the group represented by graphic formula VC wherein L is hydrogen or methyl and M is phenyl or mono-substituted phenyl and said phenyl substituent is $C_1$–$C_3$ alkyl, $C_1$–$C_3$ alkoxy or fluoro.

More preferably, B and B' are each selected from the group consisting of: (a) mono R-substituted phenyl; (b) phenyl, mono- and di-substituted phenyl, preferably substituted in the meta and/or para positions; (c) the unsubstituted, mono- and di-substituted heteroaromatic groups furanyl, benzofuran-2-yl, thienyl and benzothien-2-yl, each of said phenyl and heteroaromatic substituents in (b) and (c) being selected from the group consisting of hydroxy, $C_1$–$C_3$ alkyl, $C_1$–$C_3$ alkoxy, phenyl, indolino, fluoro and chloro; (d) the group represented by graphic formulae VA wherein E is carbon and G is oxygen, $R_{14}$ is $C_1$–$C_3$ alkyl or $C_1$–$C_3$ alkoxy; $R_{15}$ and $R_{16}$ are each hydrogen or $C_1$–$C_3$ alkyl; and q is 0 or 1.

Compounds represented by graphic formulae I, II and III may be prepared by the following steps. In Reaction A, a poly(ethylene glycol)methyl ether represented by general formula VI (wherein x is the same as for group R) or an other poly(alkylene glycol)methyl ether is reacted with toluenesulfonyl chloride represented by graphic formula VII in the presence of triethylamine (TEA) to produce the methoxy (polyethoxy)-p-toluenesulfonate represented by graphic formula VIII. Another procedure for producing the compound of graphic formula VIII is described by Bradshaw, J. S., et al, "Synthesis of Macrocyclic Acetals Containing Lipophilic Substituents", Tetrahedron, Vol. 43, No. 19, pp 4271 to 4276, 1987, which disclosure is herein incorporated by reference.

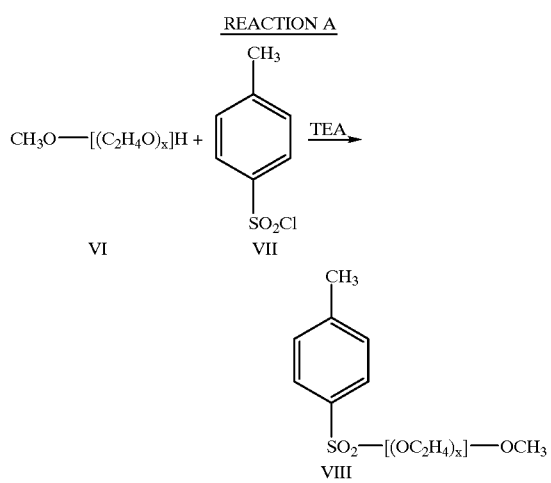

In Reaction B, the alkoxylated toluenesulfonate represented by graphic formula VIII is reacted with a naphthopyran represented by graphic formula IX in the presence of anhydrous potassium carbonate and heat to form the alkoxylated naphthopyran of graphic formula IA. Alternatively, halogenated alkoxylated alcohols may be used in place of the alkoxylated toluenesulfonate to alkylate the hydroxy functionality using the aforementioned reaction conditions. Alkylating reactions are further described in *Organic Synthesis*, Vol. 31, pages 90–93, John Wiley & Sons, Inc., New York, N.Y.

The compound represented by graphic formula IX may be prepared by coupling a substituted naphthol with a propargyl alcohol. This procedure is described in U.S. Pat. No. 5,458, 814, column 5, line 10 to column 7, line 38. The propargyl alcohol may be prepared according to the methods disclosed in U.S. Pat. No. 5,645,767, column 5, line 8 to column 6, line 30. The aforesaid patents are incorporated herein in toto by reference.

REACTION B

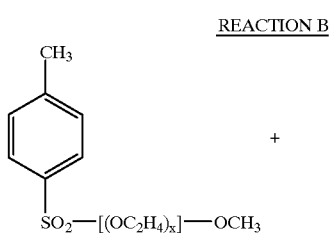

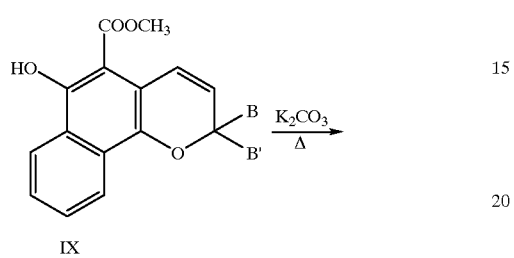

In Reaction C, a substituted naphthoic acid represented by graphic formula X is reacted with a poly(ethylene glycol) methyl ether represented by general formula VI using concentrated sulfuric acid and heat to form the alkoxylated naphthol represented by graphic formula XI. In graphic formula X, $R_2$ and $R_3$ are as previously defined. The alkoxylated naphthol represented by graphic formula XI is coupled with the propargyl alcohol represented by graphic formula XII to form the alkoxylated naphthopyran represented by graphic formula IB.

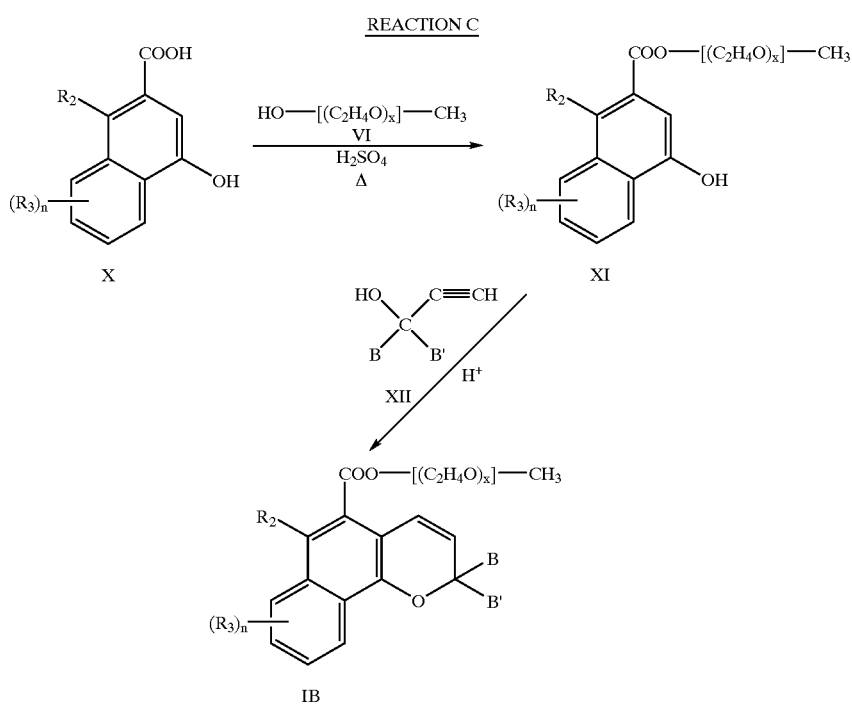

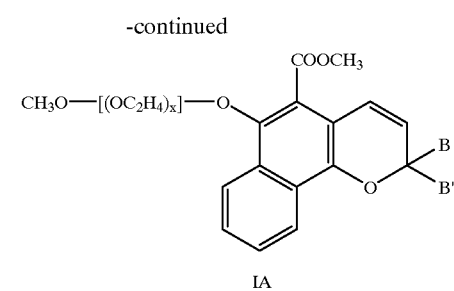

In Reaction D, the alkoxylated toluenesulfonate represented by graphic formula VIII is reacted with a hydroxy substituted benzophenone represented by graphic formula XIII to form the alkoxylated benzophenone represented by graphic formula XIV. The alkoxylated benzophenone is reacted with sodium acetylide in a suitable solvent, such as anhydrous tetrahydrofuran (THF), to form the corresponding propargyl alcohol represented by graphic formula XV. The propargyl alcohol (XV) is coupled with the substituted naphthol of graphic formula XVI to form the alkoxylated naphthopyran represented by graphic formula IIA.

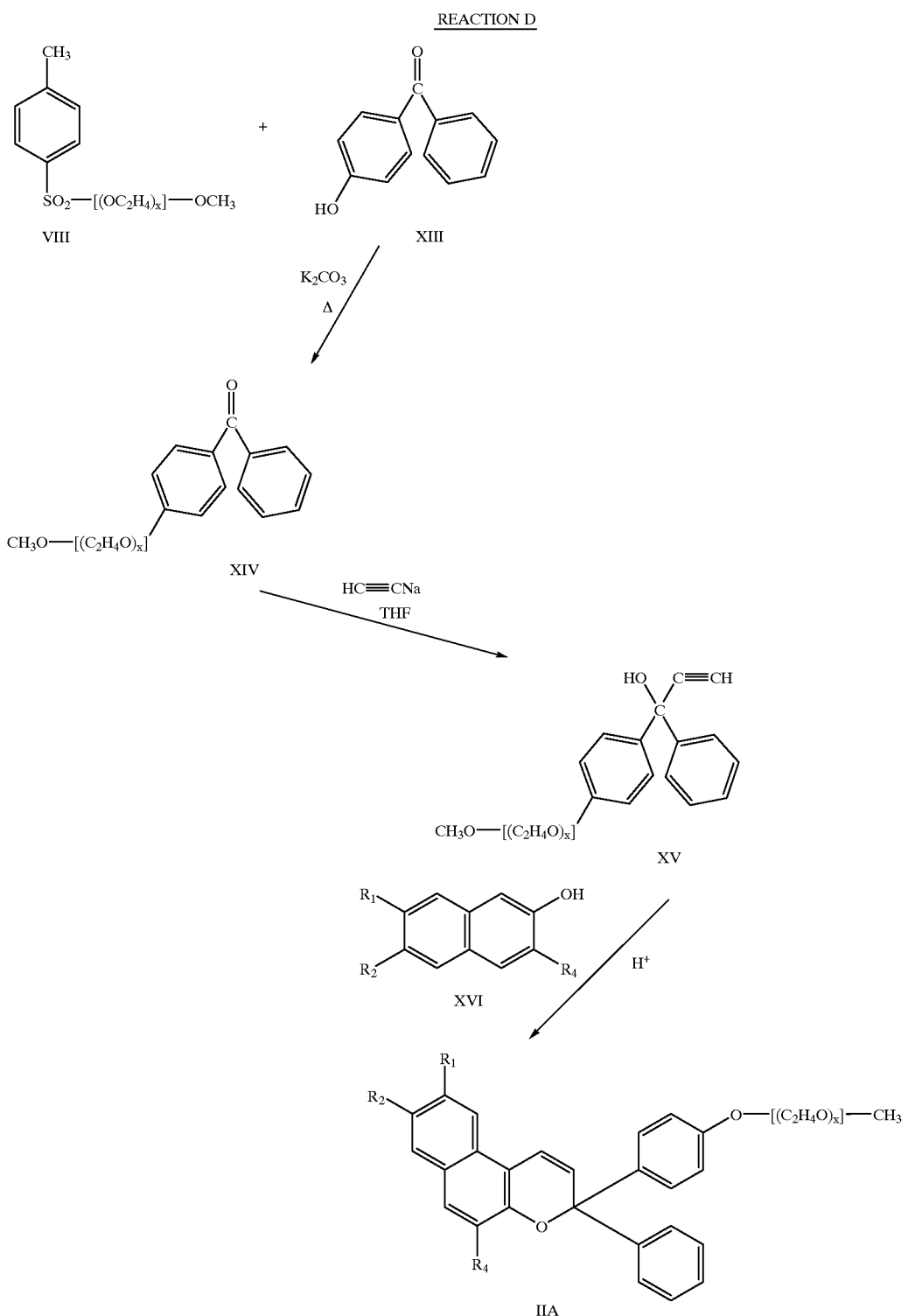

In Reaction E, the alkoxylated toluenesulfonate represented by graphic formula VIII is reacted with a hydroxy substituted acetophenone, benzophenone or benzaldehyde represented by graphic formula XVII to form the corresponding alkoxylated acetophenone, benzophenone or benzaldehyde. The compound of graphic formula XVIII is reacted with an ester of succinic acid such as dimethyl succinate represented by graphic formula XIX. Addition of the reactants to a solvent, e.g., toluene, containing potassium t-butoxide or sodium hydride as the base, yields the Stobbe condensation half ester represented by graphic formula XX. The half ester (XX) undergoes cyclodehydration in the presence of acetic anhydride to form the alkoxylated acetoxynaphthalene represented by graphic formula XXI. This product is reacted with hydrochloric acid (H⁺) and an anhydrous alcohol such as anhydrous methanol to form the corresponding naphthol represented by graphic formula XXII. The naphthol (XXII) is coupled with a propargyl alcohol represented by graphic formula XII to form the alkoxylated naphthopyran represented by graphic formula IC.
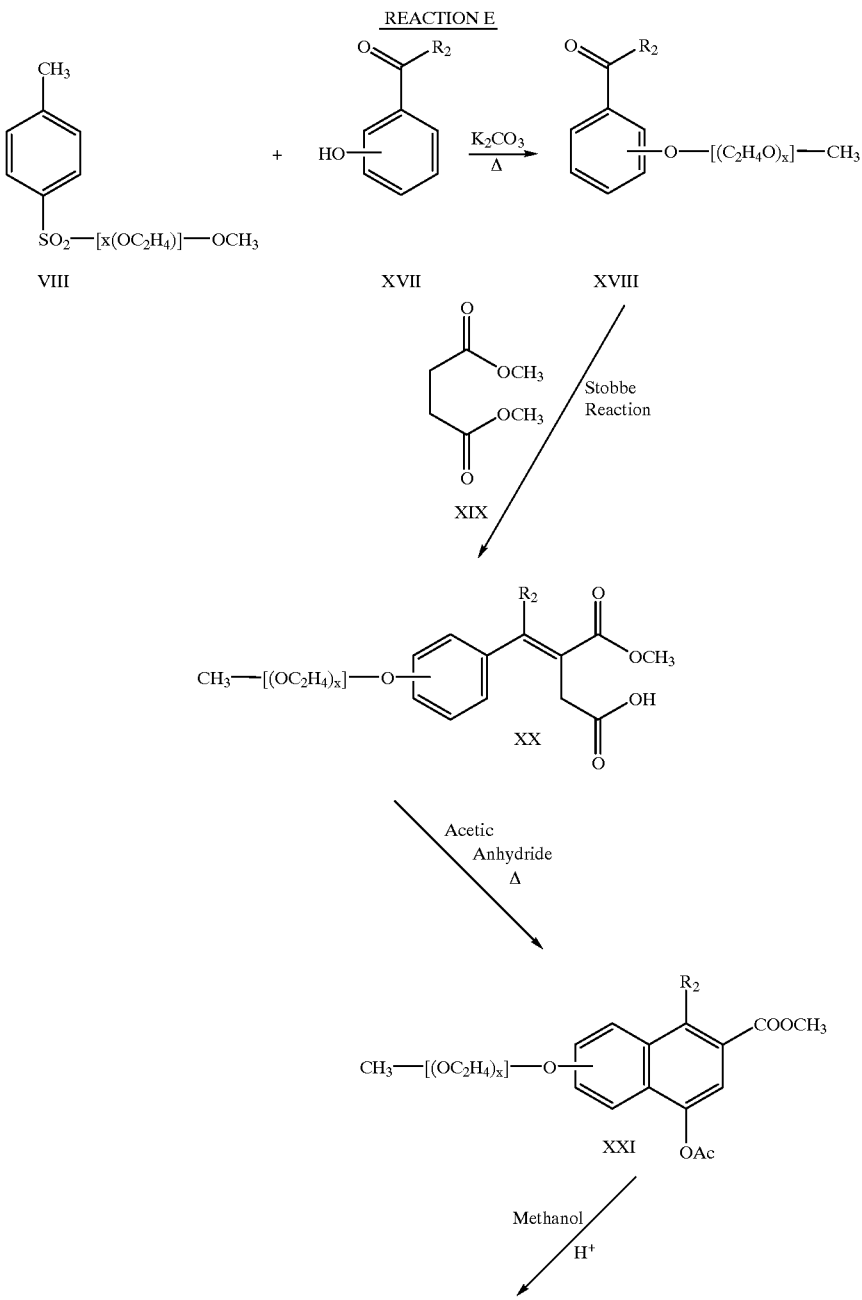

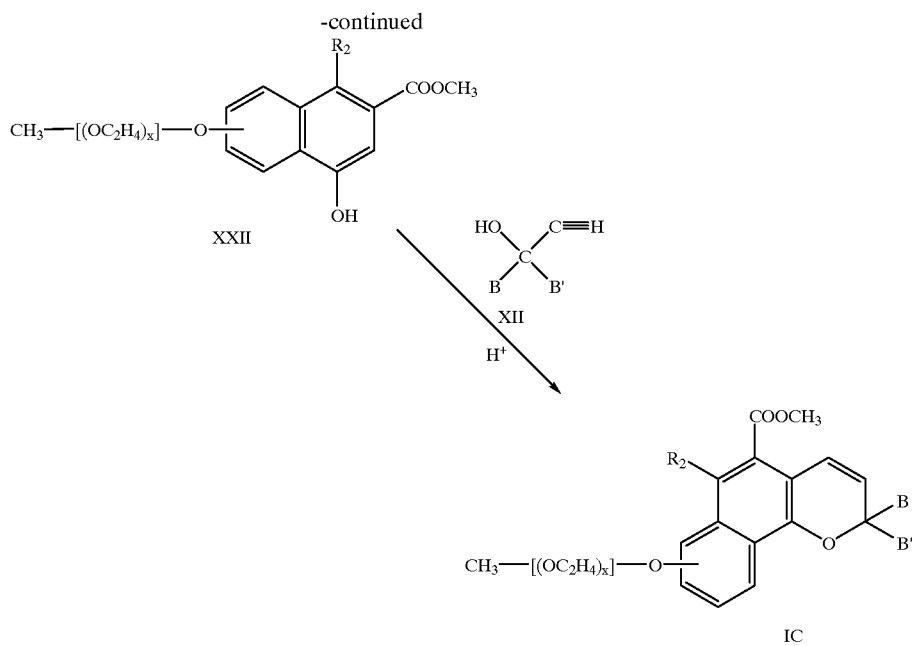

In Reaction F, the compound represented by graphic formula XXIII is reduced with lithium aluminum hydroxide (LAH) to produce the compound represented by graphic formula XXIV. Procedures for preparing the compound of graphic formula XXIII are disclosed in the afore-referenced U.S. Pat. No. 5,645,767. A poly(ethyleneglycol)methyl ether represented by general formula VI (wherein x is the same as for group R) is reacted with the compound of graphic formula XXIV using an acid (H$^+$) to form the alkoxylated indeno-fused naphthopyran of graphic formula IIIA.

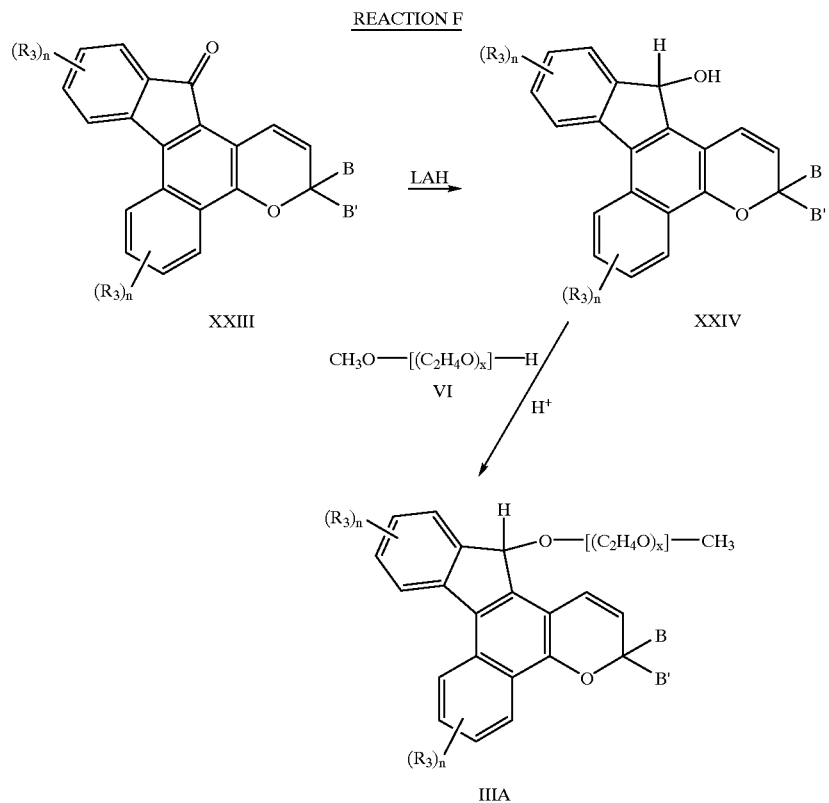

The alkoxylated naphthopyran compounds represented by graphic formulae I, IA, IB, IC, II, IIA, III and IIIA may be used in those applications in which organic photochromic substances may be employed, such as optical lenses, e.g., vision correcting ophthalmic lenses and piano lenses, face shields, goggles, visors, camera lenses, windows, automotive windshields, aircraft and automotive transparencies, e.g., T-roofs, sidelights and backlights, plastic films and sheets, textiles and coatings, e.g., coating compositions. As used herein, coating compositions include polymeric coating compositions prepared from materials such as polyurethanes, epoxy resins and other resins used to produce synthetic polymers; paints, i.e., a pigmented liquid or paste used for the decoration, protection and/or the identification of a substrate, and inks, i.e., a pigmented liquid or paste used for writing and printing on substrates, which include paper, glass, ceramics, wood, masonry, textiles, metals and polymeric organic materials. Coating compositions may be used to produce verification marks on security documents, e.g., documents such as banknotes, passport and drivers' licenses, for which authentication or verification of authenticity may be desired.

Depending on the extent of alkoxylation, the photochromic compounds of the present invention may be soluble in water, i.e., soluble in the amount of at least 1 gram per liter. The water solubility of some of the photochromic compounds of the present invention offers handling and processing advantages not achieved by water insoluble photochromic compounds. In particular, the use of hazardous organic solvents as carriers for photochromic compounds is avoided. Also avoided is the use of such solvents in cleaning excess photochromic material from the surface of polymeric substrates after an imbibition or transfer process.

The 2H-naphtho-[1,2-b]pyrans represented by graphic formula I exhibit color changes from colorless to colors ranging from yellow to red/purple. The 3H-naphtho[2,1-b] pyrans represented by graphic formula II exhibit color changes from colorless to colors ranging from yellow to orange and red. The indeno[2,1-f]naphtho[1,2-b]pyrans represented by graphic formulae III exhibit color changes from colorless to colors ranging from orange to blue/gray.

Examples of contemplated naphthopyrans within the scope of the invention are the following:

(a) 2,2-bis(4-methoxyphenyl)-5-methoxycarbonyl-6-methoxy(polyethoxy)(16EO)-[2H]-naphtho[1,2-b]pyran;

(b) 2,2-diphenyl-5-(2-(2-methoxyethoxy)ethoxycarbonyl)-6-phenyl-[2H]-naphtho[1,2-b]pyran;

(c) 2,2-diphenyl-5-(2-(2-(2-methoxyethoxy)ethoxy)ethoxycarbonyl)-6-methyl-[2H]-naphtho[1,2-b]pyran;

(d) 2,2-diphenyl-5-(2-(2-(2-methoxyethoxy)ethoxy)ethoxycarbonyl)-6-phenyl-[2H]-naphtho[1,2-b]pyran;

(e) 2-2-diphenyl-5-carbomethoxy-9-(2-(2-(2-methoxyethoxy)ethoxy)propyloxy)-[2H]-naphtho[1,2-b]pyran;

(f) 3-phenyl-3-(4-(2-(2-(2-methoxyethoxy)ethoxy)ethoxy)phenyl)-[3H]-naphtho[2,1-b]pyran;

(g) 3,3-di(4-methoxyphenyl)-6,11,13-trimethyl-13-(2-(2-(2-methoxyethoxy)ethoxy)ethoxy)-indeno[2,1-f]naphtho[1,2-b]pyran;

(h) 3-phenyl-3-(4-(2-(2-(2-methoxy-ethoxy)ethoxy)ethoxy)phenyl)-8-methoxy-9-(2-(2-(2-methoxyethoxy)ethoxy)ethoxycarbonyl)-[3H]-naphtho[2,1-b]pyran; and (i) 3-phenyl-3-(4-morpholinophenyl)-6-(2-(2-methoxyethoxy)ethoxy)-11,13-dimethyl-13-hydroxy-indeno[2,1-f]naphtho[1,2-b]pyran.

It is contemplated that the photochromic naphthopyrans of the present invention may each be used alone, in combination with other naphthopyrans of the present invention, or in combination with one or more other appropriate complementary organic photochromic materials, i.e., organic photochromic compounds having at least one activated absorption maxima within the range of between about 400 and 700 nanometers (or substances containing the same) and which color when activated to an appropriate hue.

Examples of complementary organic photochromic compounds include other naphthopyrans and indenonaphthopyrans, chromenes and oxazines, substituted 2H-phenanthro[4,3-b]pyran and 3H-phenanthro[1,2-b]pyran compounds, benzopyran compounds having substituents at the 2-position of the pyran ring and mixtures of such photochromic compounds. Such photochromic compounds are described in U.S. Pat. Nos. 3,562,172; 3,567,605; 3,578,602; 4,215,010; 4,342,668; 4,816,584; 4,818,096; 4,826,977; 4,880,667; 4,931,219; 5,066,818; 5,238,981; 5,274,132; 5,384,077; 5,405,958; 5,429,774; 5,458,814; 5,466,398; 5,514,817; 5,552,090; 5,552,091; 5,565,147; 5,573,712; 5,578,252; 5,637,262; 5,645,767; 5,656,206; 5,658,500; 5,658,501; 5,674,432 and 5,698,141. Spiro(indoline)pyrans are also described in the text, *Techniques in Chemistry*, Volume III, "Photochromism", Chapter 3, Glenn H. Brown, Editor, John Wiley and Sons, Inc., New York, 1971.

The complementary organic photochromic materials may also include polymerizable photochromic compounds, such as those disclosed in U.S. Pat. Nos. 4,719,296; 5,166,345; 5,236,958; 5,252,742; 5,359,035; and 5,488,119.

Other complementary photochromic substances contemplated are metal-dithiozonates, e.g., mercury dithizonates which are described in, for example, U.S. Pat. No. 3,361,706; and fulgides and fulgimides, e.g., the 3-furyl and 3-thienyl fulgides and fulgimides which are described in U.S. Pat. No. 4,931,220 at column 20, line 5 through column 21, line 38.

The disclosures relating to such photochromic compounds in the aforedescribed patents are incorporated herein, in toto, by reference. The photochromic articles of the present invention may contain one photochromic compound or a mixture of photochromic compounds, as desired.

The photochromic compounds of the present invention may be associated with a polymeric organic host material or other substrate by various means. They may be incorporated, i.e., dissolved and/or dispersed, into the host material and/or incorporated into a coating applied to a substrate, e.g., a polymeric coating applied to one surface of the polymeric organic host material.

Other than where otherwise indicated, all numbers expressing values, such as, wavelengths, quantities of ingredients or reaction conditions used herein are to be understood as modified in all instances by the term "about".

Each of the photochromic substances described herein may be used in amounts (or in a ratio) such that an organic host material to which the photochromic compounds or mixture of compounds is applied or in which they are incorporated exhibits a desired resultant color, e.g., a substantially neutral color when activated with unfiltered sunlight, i.e., as near a neutral color as possible given the colors of the activated photochromic compounds. Neutral gray and neutral brown colors are preferred. Further discussion of neutral colors and ways to describe such colors may be found in U.S. Pat. No. 5,645,767 column 12, line 66 to column 13, line 19.

The amount of the photochromic naphthopyrans to be applied to or incorporated into a carrier or host material is not critical provided that a sufficient amount is used to produce a photochromic effect discernible to the naked eye upon activation. Generally such amount can be described as a photochromic amount. The particular amount used depends often upon the intensity of color desired upon irradiation thereof and upon the method used to incorporate or apply the photochromic compounds. Typically, the more photochromic compound applied or incorporated, the greater is the color intensity up to a certain limit.

The relative amounts of the aforesaid photochromic compounds used will vary and depend in part upon the relative intensities of the color of the activated species of such compounds, and the ultimate color desired. Generally, the amount of total photochromic compound incorporated into or applied to a photochromic optical host material may range from about 0.05 to about 1.0, e.g., from 0.1 to about 0.45, milligrams per square centimeter of volume or surface to which the photochromic compounds is incorporated or applied. The amount of photochromic material incorporated into a coating composition may range from 0.1 to 40 weight percent based on the weight of the liquid coating composition.

The photochromic naphthopyrans of the present invention may be associated with the host material by various methods described in the art. See, for example, column 13, lines 40 to 58 of U.S. Pat. No. 5,645,767. Aqueous or organic solutions of the photochromic compounds may be used to incorporate the photochromic compounds into a polymeric organic host material or other materials such as textiles and polymeric coating compositions. Polymeric coating compositions may be applied to the substrate using a coating process such as that described in U.S. Pat. No. 3,971,872, the disclosure of which is incorporated herein by reference.

Application of the polymeric coating may be by any of the methods used in coating technology such as, for example, spray coating, spin coating, spread coating, curtain coating, dip coating, casting or roll-coating and methods used in preparing overlays, such as the method of the type described in U.S. Pat. No. 4,873,029, which is incorporated herein by reference. The application method selected also depends on the thickness of the cured coating. Coatings having a thickness ranging from 1 to 50 microns may be applied by conventional methods used in coating technology. Coatings of a thickness greater than 50 microns may require molding methods typically used for overlays.

The host material will usually be transparent, but may be translucent or even opaque. The host material need only be pervious to that portion of the electromagnetic spectrum, which activates the photochromic substance, i.e., that wavelength of ultraviolet (UV) light that produces the open or colored form of the substance and that portion of the visible spectrum that includes the absorption maximum wavelength of the substance in its UV activated form, i.e., the open form. Preferably, the host color should not be such that it masks the color of the activated form of the photochromic compounds, i.e., so the change in color is readily apparent to the observer. Compatible tints may be applied to the host material as described in U.S. Pat. No. 5,645,767 in column 13, line 59 to column 14, line 3.

Examples of polymeric organic host materials which may be used with the photochromic compounds described herein include: polymers, i.e., homopolymers and copolymers, of the bis(allyl carbonate) monomers, diethylene glycol dimethacrylate monomers, diisopropenyl benzene monomers, ethoxylated bisphenol A dimethacrylate monomers, ethylene glycol bismethacrylate monomers, poly (ethylene glycol) bismethacrylate monomers, ethoxylated phenol bismethacrylate monomers, alkoxylated polyhydric alcohol acrylate monomers, such as ethoxylated trimethylol propane triacrylate monomers, urethane acrylate monomers, such as those described in U.S. Pat. No. 5,373,033, and vinylbenzene monomers, such as those described in U.S. Pat. No. 5,475,074 and styrene; polymers, i.e., homopolymers and copolymers, of polyfunctional, e.g., mono-, di- or multi-functional, acrylate and/or methacrylate monomers, poly($C_1$–$C_{12}$ alkyl methacrylates), such as poly(methyl methacrylate), poly(oxyalkylene)dimethacrylate, poly (alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), polyurethanes, polythiourethanes, thermoplastic polycarbonates, polyesters, poly(ethylene terephthalate), polystyrene, poly (alpha methylstyrene), copoly(styrene-methyl methacrylate), copoly(styrene-acrylonitrile), polyvinylbutyral and polymers, i.e., homopolymers and copolymers, of diallylidene pentaerythritol, particularly copolymers with polyol (allyl carbonate) monomers, e.g., diethylene glycol bis(allyl carbonate), and acrylate monomers, e.g., ethyl acrylate, butyl acrylate. Further examples of polymeric organic host materials are disclosed in the U.S. Pat. No. 5,753,146, column 8, line 62 to column 10, line 34, which disclosure is incorporated herein by reference.

Transparent copolymers and blends of transparent polymers are also suitable as host materials. Preferably, the host material or substrate for the photochromic polymeric coating composition is an optically clear polymerized organic material prepared from a thermoplastic polycarbonate resin, such as the carbonate-linked resin derived from bisphenol A and phosgene, which is sold under the trademark, LEXAN; a polyester, such as the material sold under the trademark, MYLAR; a poly(methyl methacrylate), such as the material sold under the trademark, PLEXIGLAS; polymerizates of a polyol(allyl carbonate) monomer, especially diethylene glycol bis(allyl carbonate), which monomer is sold under the trademark CR-39, and polymerizates of copolymers of a polyol (allyl carbonate), e.g., diethylene glycol bis(allyl carbonate), with other copolymerizable monomeric materials, such as copolymers with vinyl acetate, e.g., copolymers of from 80–90 percent diethylene glycol bis (allyl carbonate) and 10–20 percent vinyl acetate, particularly 80–85 percent of the bis(allyl carbonate) and 15–20 percent vinyl acetate, and copolymers with a polyurethane having terminal diacrylate functionality, as described in U.S. Pat. Nos. 4,360,653 and 4,994,208; and copolymers with aliphatic urethanes, the terminal portion of which contain allyl or acrylyl functional groups, as described in U.S. Pat. No. 5,200,483; poly(vinyl acetate), polyvinylbutyral, polyurethane, polythiourethanes, polymers of members of the group consisting of diethylene glycol dimethacrylate monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol bismethacrylate monomers and ethoxylated trimethylol propane triacrylate monomers; cellulose acetate, cellulose propionate, cellulose butyrate, cellulose acetate butyrate, polystyrene and copolymers of styrene with methyl methacrylate, vinyl acetate and acrylonitrile.

More particularly, contemplated is use of the photochromic naphthopyrans of the present invention with optical organic resin monomers used to produce optically clear coatings and polymerizates, i.e., materials suitable for optical applications, such as for example lenses, i.e., plano and ophthalmic lenses. Optically clear polymerizates may have a refractive index that may range from about 1.48 to about 1.75, e.g., from about 1.495 to about 1.66. Specifically contemplated are polymerizates of optical resins sold by PPG Industries, Inc. under the CR- designation, e.g., CR-307 and CR-407.

The present invention is more particularly described in the following examples which are intended as illustrative only, since numerous modifications and variations therein will be apparent to those skilled in the art.

EXAMPLE 1

STEP 1

Poly(ethylene glycol) methyl ether (35 grams, 0.1 mole) having a number average molecular weight of approximately 350 and an equivalent of toluenesulfonyl chloride (19 grams) were added to a reaction flask containing chloroform (150 mL) and a slight excess of triethylamine (11 grams). The resulting mixture was heated to reflux temperature and maintained at that temperature overnight. After cooling to room temperature, the reaction mixture was added to a beaker containing an equal volume of water. The resulting organic layer was separated and the solvent, chloroform, was removed under vacuum to yield methoxy (polyethoxy)-p-toluenesulfonate with an average molecular weight of 504. This material was not purified but used directly in the next step.

STEP 2

The product of Step 1 (5 grams, 0.01 mole) was added to a reaction flask containing acetone (50 mL), a molar equivalent of 2,2-bis(4-methoxyphenyl)-5-methoxycarbonyl-6-hydroxy-2H-naphtho[1,2-b]pyran (4.4 grams, 0.01 mole), which is the compound of Example 1 of U.S. Pat. No. 5,458,814, and powdered potassium carbonate (2 grams). The resulting reaction mixture was heated to reflux and maintained at that temperature overnight. The solvent, acetone, was removed by vacuum and the resulting residue was dissolved in chloroform and chromatographed using a silica gel column. After the residual starting materials and by-products had eluted using chloroform elutant, the solvent was changed to a combination of 10% ethanol and 90% chloroform by volume and the desired product was recovered from the column. A nuclear magnetic resonance (NMR) spectrum showed the recovered product, approximately 2 grams of a red oil, to have a structure consistent with 2,2-bis(4-methoxyphenyl)-5-methoxycarbonyl-6-methoxy (polyethoxy)-2H-naphtho[1,2-b]pyran having an average of 16 ethoxy units.

EXAMPLE 2

STEP 1

1-Phenyl-4-hydroxy-2-naphthoic acid, 5 grams, di(ethylene glycol) methyl ether, 50 grams, and concentrated sulfuric acid, 1 gram, were added to a reaction flask. The resulting mixture was heated to near the reflux temperature (approximately 190° C.) for about 90 minutes. The resulting mixture was cooled to room temperature. Water and chloroform (200 mL of each) were added to the mixture and the organic layer was separated. The organic layer was washed twice with 200 mL water, twice with 200 mL dilute aqueous sodium bicarbonate, once again with 200 mL water and finally with 200 mL dilute aqueous hydrochloric acid. The solvent, chloroform, was removed by vacuum and the resulting residue (4 grams) was dried under a stream of air overnight and used directly in the next step.

STEP 2

The product of Step 1, 1,1-diphenyl-2-propyn-1-ol (4 grams), toluene (50 mL), and dodecylbenzene sulfonic acid (2 or 3 drops) were added to a reaction flask. The resulting mixture was heated at approximately 50° C. for four hours, cooled to room temperature and vacuum dried. The resulting residue was dissolved into a hexane:ethylacetate eluant (2:1 on a volume basis) and chromatographed using a silica gel column. The photochromic fraction was collected and the solvent removed on a rotary aspirator yielding an oil that crystallized upon standing. The recovered product (3 grams) had a melting point of 134–135° C. A nuclear magnetic resonance (NMR) spectrum showed the product to have a structure consistent with 2,2-diphenyl-5-(2-(2-methoxyethoxy)ethoxycarbonyl)-6-phenyl[2H]naphtho[1,2-b]pyran.

EXAMPLE 3

The procedure of Example 2 was followed except that 1-methyl-4-hydroxy-2-naphthoic acid was used in place of 1-phenyl-4-hydroxy-2-naphthoic acid and tri(ethylene glycol) methyl ether was used in place of di(ethylene glycol) methyl ether. A nuclear magnetic resonance (NMR) spectrum showed the product, recovered as an oil (2.5 grams), to have a structure consistent with 2,2-diphenyl-5-(2-(2-(2-methoxyethoxy)ethoxy)ethoxycarbonyl)-6-methyl-2H-naphtho[1,2b]pyran.

EXAMPLE 4

The procedure of Example 2 was followed except that tri(ethylene glycol) methyl ether was used in place of di(ethylene glycol) methyl ether. A nuclear magnetic resonance (NMR) spectrum showed the product, recovered as an oil (2.5 grams), to have a structure consistent with 2,2-diphenyl-5-(2-(2-(2-methoxyethoxy)ethoxy)ethoxycarbonyl)-6-phenyl-2H-naphtho[1,2-b]pyran.

COMPARATIVE EXAMPLE 1

CE 1 is 2,2-bis(4-methoxyphenyl)-5-methoxycarbonyl-6-methoxy-2H-naphtho[1,2-b]pyran. It may be prepared by following the procedure described for Example 2 in U.S. Pat. No. 5,458,814.

COMPARATIVE EXAMPLE 2

CE 2 is 2,2-diphenyl-5-methoxycarbonyl-6-phenyl-2H-naphtho[1,2-b]pyran. It may be prepared by following the procedure described for Example 7 in U.S. Pat. No. 5,458,814 using methyl, 1-phenyl-4-hydroxy-2-naphthoate in place of methyl,1,4-dihydroxy-2-naphthoate.

COMPARATIVE EXAMPLE 3

CE 3 is 2,2-diphenyl-5-methoxycarbonyl-6-methyl-2H-naphtho[1,2b]pyran. It may be prepared by following the procedure described for Example 8 in U.S. Pat. No. 5,458,814 using 1,1-diphenyl-2-propyn-1-ol in place of 1,1-bis(4-methoxyphenyl)-2-propyn-1-ol.

EXAMPLE 5

PART A

Testing was done with the photochromic compounds described in Examples 1 through 4 and Comparative Examples 1 through 3 in the following manner. A quantity of photochromic compound calculated to yield a 1.5×10−3 molal solution was added to a flask containing 50 grams of a monomer blend of 4 parts ethoxylated bisphenol A dimethacrylate (BPA 2EO DMA), 1 part poly(ethylene glycol) 600 dimethacrylate, and 0.033 weight percent 2,2'-azobis(2-methyl propionitrile) (AIBN). The photochromic compound was dissolved into the monomer blend by stirring and gentle heating, if necessary. After a clear solution was obtained, it was poured into a flat sheet mold having the interior dimensions of 2.2 mm×6 inches (15.24 cm)×6 inches (15.24 cm). The mold was sealed and placed in a horizontal air flow, programmable oven programmed to increase the temperature from 40° C. to 95° C. over a 5 hour interval, hold the temperature at 95° C. for 3 hours, lower it to 60° C. over a 2 hour interval and then hold it at 60° C. for 16 hours. After the mold was opened, the polymer sheet was cut using a diamond blade saw into 2 inch (5.1 centimeters) test squares.

PART B

The photochromic test squares prepared in Part A were tested for photochromic response on an optical bench. Prior to testing on the optical bench, the photochromic test squares were conditioned, i.e., exposed to 365 nanometer ultraviolet light for about 15 minutes to activate the photochromic compounds and then placed in a 76° C. oven for about 15 minutes to bleach or inactivate the photochromic compounds. The test squares were then cooled to room temperature, exposed to fluorescent room lighting for at least 2 hours and then kept covered for at least 2 hours prior to testing on an optical bench maintained at 72° F. (22.2° C.). The bench was fitted with a 250 watt Xenon arc lamp, a remote controlled shutter, a copper sulfate bath acting as a heat sink for the arc lamp, a Schott WG-320 nm cut-off filter which removes short wavelength radiation; neutral density filter(s) and a sample holder in which the square to be tested was inserted. The power output of the optical bench, i.e., the dosage of light that the sample lens would be exposed to, was calibrated with a photochromic test square used as a reference standard. This resulted in a power output ranging from 0.15 to 0.20 milliwatts per square centimeter (mW/cm2). Measurement of the power output was made using a GRASEBY Optronics Model S-371 portable photometer (Serial #21536) with a UV-A detector (Serial #22411) or comparable equipment. The UV-A detector was placed into the sample holder and the light output was measured. Adjustments to the power output were made by increasing or decreasing the lamp wattage or by adding or removing neutral density filters in the light path.

A monitoring, collimated beam of light from a tungsten lamp was passed through the square at a small angle (approximately 30°) normal to the square. After passing through the square, the light from the tungsten lamp was directed to a detector through Spectral Energy Corp. GM-200 monochromator set at the previously determined visible lambda max of the photochromic compound being measured. The output signals from the detector were processed by a radiometer.

Change in optical density ($\Delta$OD) was determined by inserting a test square in the bleached state into the sample holder, adjusting the transmittance scale to 100%, opening the shutter from the Xenon lamp to provide ultraviolet radiation to change the test square from the bleached state to an activated (i.e., darkened) state, measuring the transmittance in the activated state, and calculating the change in optical density according to the formula: $\Delta OD = \log(100/\% Ta)$, where % Ta is the percent transmittance in the activated state and the logarithm is to the base 10.

The optical properties of the photochromic compounds in the test squares are reported in Table 1. The $\Delta$OD/Min, which represents the sensitivity of the photochromic compound's response to UV light, was measured over the first five (5) seconds of UV exposure, then expressed on a per minute basis. The saturation optical density ($\Delta$OD@ Saturation) was taken under identical conditions as the $\Delta$OD/Min, except UV exposure was continued for 15 minutes. The lambda max (Vis) is the wavelength in nanometers (nm) in the visible spectrum at which the maximum absorption of the activated (colored) form of the photochromic compound in a test square occurs. The lambda max (Vis) wavelength was determined by testing the photochromic test square polymerizates of Part A in a Varian Cary 3 UV-Visible spectrophotometer. The lambda ($\lambda$) max (UV) is the wavelength in nanometers in the ultraviolet range closest to the visible spectrum at which the absorption of the photochromic compound occurs. This absorption was also determined with the same spectrophotometer. The Bleach Rate (T ½) is the time interval in seconds for the absorbance of the activated form of the photochromic compound in the test squares to reach one half the highest absorbance at room temperature (72° F., 22.2° C.) after removal of the source of activating light.

In Table 1, the results for the Example compounds should be compared to the corresponding Comparative Example as follows: Example 1 with CE1, Examples 2 and 4 with CE2, and Example 3 with CE3. The corresponding Comparative Examples have the same structure as the Example compounds except for the polyalkoxylated substituent.

TABLE 1

| Example Number | ($\lambda$) max (UV) | ($\lambda$) max (VIS) | $\Delta$OD/MIN Sensitivity | $\Delta$OD@ Saturation | Bleach Rate (T 1/2) |
| --- | --- | --- | --- | --- | --- |
| 1 | 353 | 511 | 0.19 | 0.48 | 103 |
| 2 | 348 | 486 | 0.26 | 0.67 | 167 |
| 3 | 349 | 475 | 0.24 | 0.86 | 270 |
| 4 | 348 | 486 | 0.28 | 0.67 | 165 |
| CE1 | 353 | 512 | 0.29 | 0.77 | 136 |
| CE2 | 348 | 486 | 0.28 | 0.80 | 230 |
| CE3 | 349 | 476 | 0.23 | 1.17 | 465 |

Table 1 shows that a comparison of the results for the compounds of the Examples with the results for the corresponding compounds of the Comparative Examples indicates essentially no change in color ($\lambda$ max(visible)) and a significant increase in the rate of bleaching, i.e., a decrease in the $T^{1/2}$. Specifically, the $^{1/2}$ for Example 1 is 24% less than that of CE1, the average of Examples 2 and 4 is 28% less than CE2 and for Example 3 is 42% less than CE3. Since the $T^{1/2}$ was shortened, a lower $\Delta$OD @ saturation resulted for the compounds of the Examples. There was essentially no difference in the activation wavelength ($\lambda$ max(UV)) between the Example compounds and corresponding Comparative Examples and only the Sensitivity results for Example 1 were more than 0.02 units less than the corresponding Comparative Example 1.

The present invention has been described with reference to specific details of particular embodiments thereof. It is not intended that such details be regarded as limitations upon the scope of the invention except insofar as to the extent that they are included in the accompanying claims.

We claim:

1. A naphthopyran compound represented by the following graphic formulae:

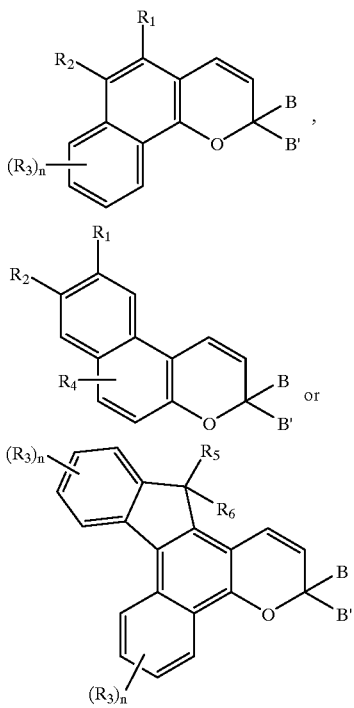

wherein, (a) $R_1$, $R_2$, $R_3$, $R_4$, $R_5$ or $R_6$ is the group R represented by the formula:

$$-A[(C_2H_4O)_x(C_3H_6O)_y(C_4H_8O)_z]D,$$

wherein —A is —C(O)O, —CH$_2$O or —O, D is $C_1$–$C_3$ alkyl, x, y and z are each a number between 0 and 50, and the sum of x, y and z is between 2 and 50, provided that only one R group is present on the naphtho or indeno portion of said naphthopyran; and provided further, that if $R_1$, $R_2$, $R_3$, $R_4$, $R_5$ or $R_6$ is not R, then:

(b) $R_1$ is hydrogen, $C_1$–$C_3$ alkyl or the group, —C(O)W, W being —OR$_7$, —N(R$_8$)R$_9$, piperidino or morpholino, wherein $R_7$ is allyl, $C_1$–$C_6$ alkyl, phenyl, mono($C_1$–$C_6$) alkyl substituted phenyl, mono($C_1$–$C_6$)alkoxy substituted phenyl, phenyl($C_1$–$C_3$)alkyl, mono($C_1$–$C_6$)alkyl substituted phenyl($C_1$–$C_3$)alkyl, mono($C_1$–$C_6$)alkoxy substituted phenyl($C_1$–$C_3$)alkyl, $C_1$–$C_6$ alkoxy($C_2$–$C_4$) alkyl or $C_1$–$C_6$ haloalkyl; $R_8$ and $R_9$ are each selected from the group consisting of $C_1$–$C_6$ alkyl, $C_5$–$C_7$ cycloalkyl, phenyl, mono-substituted phenyl and di-substituted phenyl, said phenyl substituents being $C_1$–$C_6$ alkyl or $C_1$–$C_6$ alkoxy, and said halo substituent being chloro or fluoro;

(c) $R_2$, each $R_3$, and $R_4$ are selected from the group consisting of hydrogen, $C_1$–$C_6$ alkyl, $C_3$–$C_7$ cycloalkyl, phenyl, mono-substituted phenyl, di-substituted phenyl and the groups —OR$_{10}$ and —OC(O)R$_{10}$, wherein $R_{10}$ is $C_1$–$C_6$ alkyl, phenyl($C_1$–$C_3$)-alkyl, mono($C_1$–$C_6$) alkyl substituted phenyl($C_1$–$C_3$)alkyl, mono($C_1$–$C_6$) alkoxy substituted phenyl($C_1$–$C_3$)alkyl, $C_1$–$C_6$ alkoxy ($C_2$–$C_4$)alkyl, $C_3$–$C_7$ cycloalkyl or mono($C_1$–$C_4$)alkyl substituted $C_3$–$C_7$ cycloalkyl, said phenyl substituents being $C_1$–$C_6$ alkyl or $C_1$–$C_6$ alkoxy, and n is selected from the integers 0, 1 and 2;

(d) $R_5$ and $R_6$ together form an oxo group, a spiro heterocyclic group having 2 oxygen atoms and from 3 to 6 carbon atoms including the spirocarbon atom, or $R_5$ and $R_6$ are each hydrogen, hydroxy, $C_1$–$C_6$ alkyl, $C_3$–$C_7$ cycloalkyl, allyl, phenyl, mono-substituted phenyl, benzyl, mono-substituted benzyl, chloro, fluoro, the group, —C(O)X, wherein X is hydroxy, $C_1$–$C_6$ alkyl, $C_1$–$C_6$ alkoxy, phenyl, mono-substituted phenyl, amino, mono($C_1$–$C_6$)alkylamino, or di($C_1$–$C_6$) alkylamino, or $R_5$ and $R_6$ are each the group, —OR$_{11}$, wherein $R_{11}$ is $C_1$–$C_6$ alkyl, phenyl($C_1$–$C_3$)alkyl, mono ($C_1$–$C_6$)alkyl substituted phenyl($C_1$–$C_3$)alkyl, mono ($C_1$–$C_6$)alkoxy substituted phenyl($C_1$–$C_3$)alkyl, $C_1$–$C_6$ alkoxy($C_2$–$C_4$)alkyl, $C_3$–$C_7$ cycloalkyl, mono($C_1$–$C_4$) alkyl substituted $C_3$–$C_7$ cycloalkyl, $C_1$–$C_6$ chloroalkyl, $C_1$–$C_6$ fluoroalkyl, allyl, the group, —CH(R$_{12}$)Y, wherein $R_{12}$ is hydrogen or $C_1$–$C_3$ alkyl and Y is CN, CF$_3$, or COOR$_{13}$ and $R_{13}$ is hydrogen or $C_1$–$C_3$ alkyl, or $R_{11}$ is the group, —C(O)Z, wherein Z is hydrogen, $C_1$–$C_6$ alkyl, $C_1$–$C_6$ alkoxy, the unsubstituted, mono- or di-substituted aryl groups phenyl or naphthyl, phenoxy, mono- or di-($C_1$–$C_6$)alkyl substituted phenoxy, mono- or di-($C_1$–$C_6$)alkoxy substituted phenoxy, amino, mono($C_1$–$C_6$)alkylamino, di($C_1$–$C_6$) alkylamino, phenylamino, mono- or di-($C_1$–$C_6$)alkyl substituted phenylamino, or mono- or di-($C_1$–$C_6$) alkoxy substituted phenylamino, each of said phenyl, benzyl and aryl group substituents being $C_1$–$C_6$ alkyl or $C_1$–$C_6$ alkoxy; and (e) B and B' are each selected from the group consisting of:

(i) mono R-substituted phenyl;

(ii) the unsubstituted, mono-, di- and tri-substituted aryl groups, phenyl and naphthyl;

(iii) the unsubstituted, mono- and di-substituted hetroaromatic groups pyridyl, furanyl, benzofuran-2-yl, benzofuran-3-yl, thienyl, benzothien-2-yl, benzothien-3-yl, dibenzofuranyl, dibenzothienyl, carbazolyl and fluorenyl, each of said aryl and heteroaromatic substituents in (e)(ii) and (iii) being selected from the group consisting of hydroxy, aryl, mono($C_1$–$C_6$)alkoxyaryl, di($C_1$–$C_6$)alkoxyaryl, mono($C_1$–$C_6$)alkylaryl, di($C_1$–$C_6$)alkylaryl, chloroaryl, fluoroaryl, $C_3$–$C_7$ cycloalkylaryl, $C_3$–$C_7$ cycloalkyl, $C_3$–$C_7$ cycloalkyloxy, $C_3$–$C_7$ cycloalkyloxy($C_1$–$C_6$)alkyl, $C_3$–$C_7$ cycloalkyloxy ($C_1$–$C_6$)alkoxy, aryl($C_1$–$C_6$)alkyl, aryl($C_1$–$C_6$) alkoxy, aryloxy, aryloxy($C_1$–$C_6$)alkyl, aryloxy ($C_1$–$C_6$)alkoxy, mono- and di-($C_1$–$C_6$)alkylaryl ($C_1$–$C_6$)alkyl, mono- and di-($C_1$–$C_6$)alkoxyaryl ($C_1$–$C_6$)alkyl, mono- and di-($C_1$–$C_6$)alkylaryl ($C_1$–$C_6$)alkoxy, mono- and di-($C_1$–$C_6$)alkoxyaryl ($C_1$–$C_6$)alkoxy, amino, mono($C_1$–$C_6$)alkylamino, di($C_1$–$C_6$)alkylamino, diarylamino, N-($C_1$–$C_6$) alkylpiperazino, N-arylpiperazino, aziridino, indolino, piperidino, arylpiperidino, morpholino, thiomorpholino, tetrahydroquinolino, tetrahydroisoquinolino, pyrryl, $C_1$–$C_6$ alkyl, $C_1$–$C_6$ chloroalkyl, $C_1$–$C_6$ fluoroalkyl, $C_1$–$C_6$ alkoxy, mono ($C_1$–$C_6$)alkoxy($C_1$–$C_4$)alkyl, acryloxy, methacryloxy, bromo, chloro and fluoro;

(iv) the groups represented by the following graphic formulae:

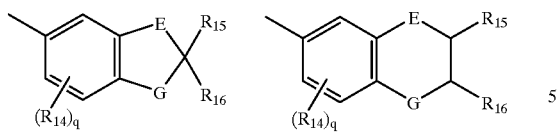

wherein E is carbon or oxygen and G is oxygen or substituted nitrogen, provided that when G is substituted nitrogen, E is carbon, said nitrogen substituents being selected from the group consisting of hydrogen, $C_1$–$C_6$ alkyl and $C_2$–$C_6$ acyl; each $R_{14}$ is $C_1$–$C_6$ alkyl, $C_1$–$C_6$ alkoxy, hydroxy, chloro or fluoro; $R_{15}$ and $R_{16}$ are each hydrogen or $C_1$–$C_6$ alkyl; and q is the integer 0, 1 or 2;

(v) $C_1$–$C_6$ alkyl, $C_1$–$C_6$ chloroalkyl, $C_1$–$C_6$ fluoroalkyl, $C_1$–$C_6$ alkoxy($C_1$–$C_4$)alkyl; and (vi) the group represented by the following graphic formula:

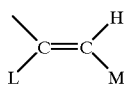

wherein L is hydrogen or $C_1$–$C_4$ alkyl and M is selected from the unsubstituted, mono-, and di-substituted members of the group consisting of naphthyl, phenyl, furanyl and thienyl, each of said group substituents being $C_1$–$C_4$ alkyl, $C_1$–$C_4$ alkoxy, fluoro or chloro.

2. The naphthopyran of claim 1 wherein (a) $R_1$, $R_2$, $R_3$, $R_4$, $R_5$ or $R_6$ is the group R, x and y are each a number between 0 and 50, z is 0 and the sum of x and y is between 2 and 50; provided that when $R_1$, $R_2$, $R_3$, $R_4$, $R_5$ or $R_6$ is not R, then:

(b) $R_1$ is the group, —C(O)W, W being —$OR_7$ or —N($R_8$)$R_9$, wherein $R_7$ is $C_1$–$C_4$ alkyl, phenyl, mono($C_2$–$C_4$)alkyl substituted phenyl, mono($C_1$–$C_4$)alkoxy substituted phenyl, phenyl($C_1$–$C_2$)alkyl, mono($C_1$–$C_4$) alkyl substituted phenyl($C_1$–$C_2$)alkyl, mono($C_1$–$C_4$) alkoxy substituted phenyl($C_1$–$C_2$)alkyl, mono($C_1$–$C_4$) alkoxy($C_2$–$C_3$)alkyl or $C_1$–$C_4$ haloalkyl; $R_8$ and $R_9$ are each selected from the group consisting of $C_1$–$C_4$ alkyl, $C_5$–$C_7$ cycloalkyl, phenyl, mono-substituted phenyl and di-substituted phenyl, said phenyl substituents being $C_1$–$C_4$ alkyl or $C_1$–$C_4$ alkoxy, said halo substituents being chloro or fluoro;

(c) $R_2$, each $R_3$, and $R_4$ are selected from the group consisting of hydrogen, $C_1$–$C_3$ alkyl, $C_3$–$C_5$ cycloalkyl, phenyl, mono-substituted phenyl, di-substituted phenyl and the group —$OR_{10}$, wherein $R_{10}$ is $C_1$–$C_4$ alkyl, phenyl($C_1$–$C_2$)alkyl, mono($C_1$–$C_4$)alkyl substituted phenyl($C_1$–$C_2$)alkyl, mono($C_1$–$C_4$)alkoxy substituted phenyl($C_1$–$C_2$)alkyl, $C_1$–$C_4$ alkoxy($C_2$–$C_4$)alkyl, $C_5$–$C_7$ cycloalkyl or mono($C_1$–$C_3$)alkyl substituted $C_5$–$C_7$ cycloalkyl and said phenyl substituents being $C_1$–$C_3$ alkyl or $C_1$–$C_3$ alkoxy;

(d) $R_5$ and $R_6$ are each selected from the group consisting of hydrogen, hydroxy, $C_1$–$C_4$ alkyl, $C_3$–$C_6$ cycloalkyl, chloro, fluoro and the group, —$OR_{11}$, wherein $R_{11}$ is $C_1$–$C_3$ alkyl, phenyl($C_1$–$C_2$)alkyl, mono($C_1$–$C_3$)alkyl substituted phenyl($C_1$–$C_3$)alkyl, mono($C_1$–$C_3$)alkoxy substituted phenyl($C_1$–$C_3$)alkyl, $C_1$–$C_3$ alkoxy($C_2$–$C_4$) alkyl, $C_1$–$C_3$ chloroalkyl, $C_1$–$C_3$ fluoroalkyl, the group, —CH($R_{12}$)Y, wherein $R_{12}$ is hydrogen or $C_1$–$C_2$ alkyl and Y is CN or COO$R_{13}$, and $R_{13}$ is hydrogen or $C_1$–$C_2$ alkyl, or $R_{11}$ is the group, —C(O)Z, wherein Z is hydrogen, $C_1$–$C_3$ alkyl, $C_1$–$C_3$ alkoxy, phenyl, naphthyl, mono-substituted aryl groups, phenyl or naphthyl, phenoxy, mono- or di-($C_1$–$C_3$)alkyl substituted phenoxy, mono- or di-($C_1$–$C_3$)alkoxy substituted phenoxy, mono($C_1$–$C_3$)alkylamino, phenylamino, mono- or di-($C_1$–$C_3$)alkyl substituted phenylamino, or mono- or di-($C_1$–$C_3$)alkoxy substituted phenylamino, and said aryl substituents being $C_1$–$C_3$ alkyl or $C_1$–$C_3$ alkoxy;

(e) B and B' are each selected from the group consisting of:

(i) mono R-substituted phenyl;

(ii) phenyl, mono-substituted and di-substituted phenyl;

(iii) the unsubstituted, mono- and di-substituted heteroaromatic groups furanyl, benzofuran-2-yl, thienyl, benzothien-2-yl, dibenzofuran-2-yl, and dibenzothien-2-yl, each of said phenyl and heteroaromatic substituents in (e) (ii) and (iii) being selected from the group consisting of hydroxy, aryl, arlyoxy, aryl($C_1$–$C_3$)alkyl, amino, mono($C_1$–$C_3$) alkylamino, di($C_1$–$C_3$)alkylamino, N-($C_1$–$C_3$) alkylpiperazino, indolino, piperidino, morpholino, pyrryl, $C_1$–$C_3$ alkyl, $C_1$–$C_3$ chloroalkyl, $C_1$–$C_3$ fluoroalkyl, $C_1$–$C_3$ alkoxy, mono($C_1$–$C_3$)alkoxy ($C_1$–$C_3$)alkyl, chloro and fluoro;

(iv) the groups represented by the following graphic formulae:

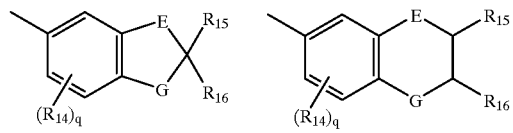

wherein E is carbon and G is oxygen, $R_{14}$ is $C_1$–$C_3$ alkyl or $C_1$–$C_3$ alkoxy; $R_{15}$ and $R_{16}$ are each hydrogen or $C_1$–$C_4$ alkyl; and q is 0 or 1;

(v) $C_1$–$C_4$ alkyl;

(vi) the group represented by the following graphic formula:

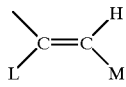

wherein L is hydrogen or methyl and M is phenyl or mono-substituted phenyl, said phenyl substituents being $C_1$–$C_3$ alkyl, $C_1$–$C_3$ alkoxy or fluoro.

3. The naphthopyran of claim 2 wherein:

(a) $R_1$, $R_2$, $R_3$, $R_4$, $R_5$ or $R_6$ is the group R and x is a number between 2 and 50, y and z are each 0; provided that when $R_1$, $R_2$, $R_3$, $R_4$, $R_5$ or $R_6$ is not R, then:

(b) $R_1$ is the group, —C(O)W, wherein W is the group, —$OR_7$, and $R_7$ is $C_1$–$C_3$ alkyl;

(c) $R_2$, each $R_3$, and $R_4$ are selected from the group consisting of hydrogen, $C_1$–$C_3$ alkyl, phenyl, mono-substituted phenyl, di-substituted phenyl and the group, $OR_{10}$, wherein $R_{10}$ is $C_1$–$C_3$ alkyl and said phenyl substituents being methyl or methoxy;

(d) $R_5$ and $R_6$ are each hydrogen, hydroxy, $C_1$–$C_4$ alkyl, or the group, —$OR_{11}$, wherein $R_{11}$ is $C_1$–$C_3$ alkyl;

(e) B and B' are each selected from the group consisting of:

(i) mono R-substituted phenyl;
(ii) phenyl, mono- and di-substituted phenyl;
(iii) the unsubstituted, mono- and di-substituted heteroaromatic groups furanyl, benzofuran-2-yl, thienyl and benzothien-2-yl, each of said phenyl and heteroaromatic substituents in (e) (ii) and (iii) being selected from the group consisting of hydroxy, $C_1$–$C_3$ alkyl, $C_1$–$C_3$ alkoxy, phenyl, indolino, fluoro and chloro; and
(iv) the group represented by the following graphic formula:

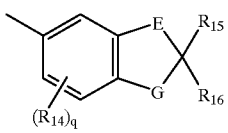

wherein E is carbon and G is oxygen, $R_{14}$ is $C_1$–$C_3$ alkyl or $C_1$–$C_3$ alkoxy; $R_{15}$ and $R_{16}$ are each hydrogen or $C_1$–$C_3$ alkyl; and q is 0 or 1.

4. A naphthopyran compound selected from the group consisting of:
(a) 2,2-bis(4-methoxyphenyl)-5-methoxycarbonyl-6-methoxy(polyethoxy)(16EO)-2H-naphtho[1,2-b]pyran;
(b) 2,2-diphenyl-5-(2-(2-methoxyethoxy)ethoxycarbonyl)-6-phenyl-2H-naphtho[1,2-b]pyran;
(c) 2,2-diphenyl-5-(2-(2-(2-methoxyethoxy)ethoxy)ethoxycarbonyl)-6-methyl-2H-naphtho[1,2-b]pyran;
(d) 2,2-diphenyl-5-(2-(2-(2-methoxyethoxy)ethoxy)ethoxycarbonyl)-6-phenyl-2H-naphtho[1,2-b]pyran;
(e) 2-2-diphenyl-5-carbomethoxy-9-(2-(2-(2-methoxyethoxy)ethoxy)propyloxy)-2H-naphtho[1,2-b]pyran;
(f) 3-phenyl-3-(4-(2-(2-(2-methoxyethoxy)ethoxy)ethoxy)phenyl)-3H-naphtho[2,1-b]pyran;
(g) 3,3-di(4-methoxyphenyl)-6,11,13-trimethyl-13-(2-(2-(2-methoxyethoxy)ethoxy)ethoxy)-indeno[2,1-f]naphtho[1,2-b]pyran;
(h) 3-phenyl-3-(4-(2-(2-(2-methoxyethoxy)ethoxy)ethoxy)phenyl)-8-methoxy-9-(2-(2-(2-methoxyethyloxy)ethyloxy)ethyloxycarbonyl)-3H-naphtho[2,1-b]pyran; and
(i) 3-phenyl-3-(4-morpholinophenyl)-6-(2-(2-methoxyethoxy)ethoxy)-11,13-dimethyl-13-hydroxy-indeno[2,1-f]naphtho[1,2-b]pyran.

5. A photochromic article comprising in combination, a polymeric organic host material and a photochromic amount of the naphthopyran compound of claim 1.

6. The photochromic article of claim 5 wherein the polymeric organic host material is selected from the group consisting of polyacrylates, polymethacrylates, poly($C_1$–$C_{12}$) alkyl methacrylates, polyoxy(alkylene methacrylates), poly (alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonates, polyesters, polyurethanes, polythiourethanes, poly(ethylene terephthalate), polystyrene, poly(alpha methylstyrene), copoly(styrene-methylmethacrylate), copoly(styrene-acrylonitrile), polyvinylbutyral and polymers of members of the group consisting of polyol(allyl carbonate) monomers, polyfunctional acrylate monomers, polyfunctional methacrylate monomers, diethylene glycol dimethacrylate monomers, diisopropenyl benzene monomers, alkoxylated polyhydric alcohol monomers and diallylidene pentaerythritol monomers.

7. The photochromic article of claim 6 wherein the polymeric organic material is a homopolymer or copolymer of monomer(s) selected from the group consisting of acrylates, methacrylates, methyl methacrylate, ethylene glycol bis methacrylate, ethoxylated bisphenol A dimethacrylate, vinyl acetate, vinylbutyral, urethane, thiourethane, diethylene glycol bis(allyl carbonate), diethylene glycol dimethacrylate, diisopropenyl benzene, and ethoxylated trimethylol propane triacrylate.

8. The photochromic article of claim 5 wherein the photochromic compound is present in an amount of from 0.05 to 1.0 milligram per square centimeter of polymeric organic host material surface to which the photochromic substance(s) is incorporated or applied.

9. The photochromic article of claim 5 wherein said polymeric organic host material is an optical element.

10. The photochromic article of claim 9 wherein said optical element is a lens.

11. A photochromic article comprising a polymeric organic host material selected from the group consisting of poly(methyl methacrylate), poly(ethylene glycol bismethacrylate), poly(ethoxylated bisphenol A dimethacrylate), thermoplastic polycarbonate, poly(vinyl acetate), polyvinylbutyral, polyurethane and polymers of members of the group consisting of diethylene glycol bis (allyl carbonate) monomers, diethylene glycol dimethacrylate monomers, ethoxylated phenol bismethacrylate monomers, diisopropenyl benzene monomers and ethoxylated trimethylol propane triacrylate monomers, and a photochromic amount of the naphthopyran compound of claim 3.

12. A photochromic article comprising, in combination, a solid substrate and a photochromic amount of each of (a) at least one naphthopyran compound of claim 1, and (b) at least one other organic photochromic compound having at least one activated absorption maxima within the range of between 400 and 700 nanometers.

13. A photochromic article comprising a polymerizate of an optical organic resin monomer and a photochromic amount of the naphthopyran compound of claim 1.

14. The photochromic article of claim 13 wherein the refractive index of the polymerizate is from about 1.48 to about 1.75.

15. The photochromic article of claim 13 wherein the polymerizate is an optical element.

16. The photochromic article of claim 15 wherein said optical element is a lens.

17. A photochromic article comprising, in combination, a solid substrate and on at least one surface thereof a cured coating of a coating composition having a photochromic amount of the naphthopyran compound of claim 1.

18. The photochromic article of claim 17 wherein said coating composition is selected from the group consisting of a polymeric coating composition, paint and ink.

19. The photochromic article of claim 17 wherein the substrate is selected from the group consisting of glass, masonry, textiles, ceramics, metals, wood, paper and polymeric organic materials.

* * * * *